United States Patent [19]
Morin, Jr. et al.

[11] Patent Number: 6,013,674
[45] Date of Patent: Jan. 11, 2000

[54] CELL ADHESION INHIBITORS

[75] Inventors: John Michael Morin, Jr., Brownsburg; Michael Dean Kinnick, Indianapolis; Robert Theodore Vasileff, Indianapolis; William Thomas Jackson, Indianapolis, all of Ind.

[73] Assignee: Eli Lilly and Company, Indianapolis, Ind.

[21] Appl. No.: 09/071,684

[22] Filed: May 1, 1998

Related U.S. Application Data

[60] Provisional application No. 60/048,263, Jun. 2, 1997.

[51] Int. Cl.$^7$ .................................................. A61K 31/165
[52] U.S. Cl. ........................... 514/621; 514/617; 514/821; 514/825; 514/826; 514/863; 514/886; 514/908; 514/927
[58] Field of Search ..................................... 514/617, 621, 514/821, 825, 826, 863, 886, 908, 927; 564/172, 180

[56] References Cited

U.S. PATENT DOCUMENTS

| | | | |
|---|---|---|---|
| 3,453,287 | 7/1969 | Campaigne et al. | 260/326.5 |
| 3,622,623 | 11/1971 | Shen et al. | 260/515 |
| 3,763,229 | 10/1973 | Noguchi et al. | 564/180 |
| 3,822,310 | 7/1974 | Shen et al. | 564/180 |
| 3,932,498 | 1/1976 | Shen et al. | 260/515 |
| 3,956,363 | 5/1976 | Shen et al. | 260/479 |
| 3,976,634 | 8/1976 | Nadelson et al. | 260/239 |
| 3,985,729 | 10/1976 | Houlihan et al. | 260/239 |
| 4,760,086 | 7/1988 | Tischler et al. | 514/443 |
| 5,208,253 | 5/1993 | Boschelli et al. | 514/443 |
| 5,521,213 | 5/1996 | Prasit et al. | 514/443 |

FOREIGN PATENT DOCUMENTS

| | | |
|---|---|---|
| 160 408 A1 | 11/1985 | European Pat. Off. . |
| 566 446 A1 | 10/1993 | European Pat. Off. . |
| WO 93/08799 | 5/1993 | WIPO . |

OTHER PUBLICATIONS

Moussa, et al., "Polycyclic aromatic compounds, synthesis and biological screening of some new naphthalene, 1–indenone and benzo[c]fluorenone compounds", Journal of Polish Chemistry, vol. 55, No. 11, 1981, pp. 2445–2456.

Barvian et al., "1–Oxo–3–aryl–1H–Indene–2–carboxylic acid derivatives as selective inhibitors of fibroplast growth factor receptor–1 tyrosin kinase", Biorganic and Medicinal Chemistry Letters, vol. 7, No. 22, 1997, pp. 2903–2908.

Boschelli, et al., "3–Alkoxybenzo[b]thiophene–2–carboxamides as Inhibitors of Neutrophil–Endothelial Cell Adhesion", Journal of Medicinal Chemistry, vol. 37, No. 6, Mar. 18, 1994, pp. 717–718.

Smith, et al., "Recognition of an Endothelial Determinant for CD18–dependent Human Neutrophil Adherence and Transendothelial Migration", J. Clin. Invest., vol. 82, Nov. 1988, pp. 1746–1756.

Wright, et al., "Selective regulation of human neutrophil functions by the cell activation inhibitor CI–959", Journal of Leukocyte Biology, vol. 55, Apr. 1994, pp. 443–451.

Campaigne, et al., "Cyclization of Ylidenemalononitriles. X. Synthesis of Benzazapropellane Derivatives from α–Cyano–β–chloroalkylcinnamonitriles (1a)", Journal of Heterocyclic Chemistry, vol. 14, No. 8, Dec. 1977, pp. 1337–1345.

Bestmann, et al., "Synthesen von cyclischen Verbindungen aus Triphenyl[(phenylimino)ethenyliden]phosphoran and Oxocarbonsäuren—Eine neue Anellierungsmethodik", Chem Ber., 118, pp. 2640–2658 (1985).

*Primary Examiner*—Shailendra Kumar
*Attorney, Agent, or Firm*—Scott Alexander McNeil; Brian P. Barrett; Janelle D. Strode

[57] ABSTRACT

This invention provides novel indenone derivatives, their pharmaceutical formulations and their use for the inhibition of leukocyte adherence to cells.

27 Claims, No Drawings

CELL ADHESION INHIBITORS

This application claims priority to provisional application Serial No. 60/048,263 filed Jun. 2, 1997.

This invention relates to novel indenone amides and salts thereof, which inhibit leukocyte adhesion to endothelial cells and are useful in the treatment of inflammatory diseases and other conditions, such as rheumatoid arthritis, asthma, psoriasis, respiratory distress syndrome, Alzheimer's disease, reperfusion injury, ischemia, stroke, ulcerative colitis, vasculitis, and inflammatory bowel disease. This invention also provides therapeutic compositions and methods for treating said diseases and conditions.

Adherence of leukocytes to vascular endothelium is essential to the pathogenesis of inflammation. Leukocyte adherence to vascular endothelium is known to precede the transendothelial migration of leukocytes into surrounding tissue and ensuing tissue damage. An important step for leukocyte recruitment is mediated by expression of specific adhesion receptors on the surface of vascular endothelial cells. The following major adhesion receptors have been identified: vascular cell adhesion molecule-1 (VCAM-1), intercellular adhesion molecule-1 (ICAM-1) and E-selectin. Compounds that reportedly prevent leukocyte adhesion to endothelial cells and are useful in treating certain inflammatory diseases are generally 3-alkyloxy-, 3-aryloxy-, and arylalkoxybenzo[b]thiophene-2-carboxamides derivatives such as those in U.S. Pat. No. 5,208,253 and Boschelli, D. H., et al., J. Med. Chem., 37,717–18 (1994).

The indenone amides of the present invention have been shown, in vitro, to inhibit neutrophil adhesion to keyhole limpet hemocyanin (KLH) and to inhibit human neutrophils from adhering to ICAM-1 bearing endothelial cells. Accordingly, this invention provides a series of novel indenone amides which inhibit leukocyte adhesion to endothelial cells and are useful in the treatment of inflammatory diseases and conditions. This invention also provides therapeutic compositions and provides methods for treating said diseases and conditions.

SUMMARY OF THE INVENTION

An aspect of the invention provides methods for treating inflammatory diseases and conditions mediated by inhibiting the adhesion of leukocytes to endothelial cells, comprising administering to a mammal in need thereof, a pharmaceutical amount of a compound of the formula I:

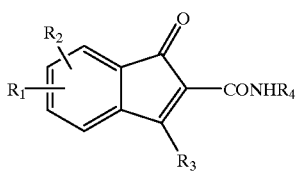

I where $R_1$ and $R_2$ are each independently hydrogen, hydroxy, nitro, amino, $C_1$–$C_4$ alkyl, $C_1$–$C_4$ alkoxy or halo; $R_3$ is hydrogen, hydroxy, $C_1$–$C_6$ alkyl, $C_2$–$C_6$ alkenyl, $C_2$–$C_6$ alkynyl, $C_3$–$C_6$ cycloalkyl, $C_1$–$C_6$ alkoxy, halo, halo($C_1$–$C_6$ alkyl) or unsubstituted or substituted phenyl; and $R_4$ is hydrogen or $C_1$–$C_4$ alkyl, or a pharmaceutically acceptable salt or solvate thereof.

An other aspect of this invention provides pharmaceutical compositions containing these compounds as active ingredients for treating inflammatory diseases and other conditions, including rheumatoid arthritis, asthma, psoriasis, stroke, Alzheimer's disease, respiratory distress syndrome, reperfusion injury, ischemia, ulcerative colitis, vasculitis, and inflammatory bowel disease.

Still another aspect of this invention provides novel indenone amide compounds of the formula Ia:

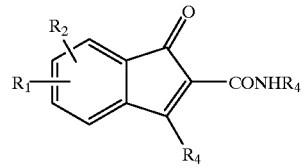

Ia where $R_1$ and $R_2$ are each independently hydrogen, hydroxy, nitro, amino, $C_1$–$C_4$ alkyl, $C_1$–$C_4$ alkoxy or halo; $R_3$ is hydrogen, hydroxy, $C_1$–$C_6$ alkyl, $C_2$–$C_6$ alkenyl, $C_2$–$C_6$ alkynyl, $C_3$–$C_6$ cycloalkyl, $C_1$–$C_6$ alkoxy, halo, halo($C_1$–$C_6$ alkyl) or unsubstituted or substituted phenyl; and $R_4$ is hydrogen or $C_1$–$C_4$ alkyl, or a pharmaceutically acceptable salt or solvate thereof; provided that, when $R_1$, $R_2$ and $R_4$ are each hydrogen, $R_3$ is other than $C_1$–$C_4$ alkyl, halo($C_1$–$C_6$ alkyl), cyclopropyl or phenyl.

DETAILED DESCRIPTION

The various positions on the indenone ring are indicated below:

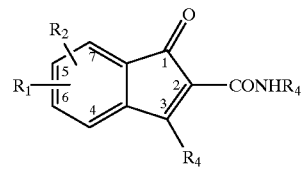

where $R_1$ and $R_2$ each occupies one of the 4, 5, 6 or 7 positions.

The following compounds illustrate compounds contemplated within the scope of formula I:

2-carboxamidoindenone
2-carboxamido-3-hydroxyindenone
2-carboxamido-3-methylindenone
2-carboxamido-3-methoxyindenone
2-carboxamido-3-ethoxyindenone
2-carboxamido-3-ethylindenone
2-carboxamido-3-propylindenone
2-carboxamido-3-isopropylindenone
2-carboxamido-3-(3-chloropropyl)indenone
2-carboxamido-3-butylindenone
2-carboxamido-3-isobutylindenone
2-carboxamido-3-t-butylindenone
2-carboxamido-3-(3-methylbutyl)indenone
2-carboxamido-3-(1-ethylpropyl)indenone
2-carboxamido-3-hexylindenone
2-carboxamido-3-(4-methylpentyl)indenone
2-carboxamido-3-pentylindenone
2-carboxamido-3-ethenylindenone
2-carboxamido-3-(2-buten-1-yl)indenone
2-carboxamido-3-(3-buten-1-yl)indenone
2-carboxamido-3-ethynylindenone
2-carboxamido-3-(2-propynyl)indenone
2-carboxamido-3-(2-butynyl)indenone
2-carboxamido-3-cyclopropylindenone
2-carboxamido-3-cyclobutylindenone
2-carboxamido-3-cyclopentylindenone 2-carboxamido-3-phenylindenone
2-carboxamido-3-cyclohexylindenone
2-carboxamido-3-(5-chloropentyl)indenone
2-methylcarboxamidoindenone
2-methylcarboxamido-3-hydroxyindenone
2-methylcarboxamido-3-methylindenone
2-methylcarboxamido-3-ethylindenone
2-methylcarboxamido-3-propylindenone
2-methylcarboxamido-3-isopropylindenone
2-methylcarboxamido-3-(3-chloropropyl)indenone
2-methylcarboxamido-3-butylindenone
2-methylcarboxamido-3-isobutylindenone
2-methylcarboxamido-3-t-butylindenone
2-methylcarboxamido-3-(3-methylbutyl)indenone
2-methylcarboxamido-3-(1-ethylpropyl)indenone
2-methylcarboxamido-3-hexylindenone
2-methylcarboxamido-3-(4-methylpentyl)indenone
2-methylcarboxamido-3-pentylindenone
2-methylcarboxamido-3-ethenylindenone
2-methylcarboxamido-3-(2-buten-1-yl)indenone
2-methylcarboxamido-3-(3-buten-1-yl)indenone
2-methylcarboxamido-3-ethynylindenone
2-methylcarboxamido-3-(2-propynyl)indenone
2-methylcarboxamido-3-(2-butynyl)indenone
2-methylcarboxamido-3-cyclopropylindenone
2-methylcarboxamido-3-cyclopentylindenone
2-methylcarboxamido-3-cyclohexylindenone
2-methylcarboxamido-3-(5-chloropentyl)indenone
2-methylcarboxamido-3-phenylindenone
2-methylcarboxamido-3-(1-chloro-2-methylbutyl)indenone
2-methylcarboxamido-3-(1-bromo-2-methylbutyl)indenone
2-methylcarboxamido-3-(1-iodo-2-methylbutyl)indenone
2-methylcarboxamido-3-(1-chloro-2-methylpentyl)indenone
2-methylcarboxamido-3-(1-bromo-2-ethylbutyl)indenone
2-methylcarboxamido-3-(4-ethylphenyl) indenone
2-methylcarboxamido-3-(2-ethylphenyl)indenone
2-methylcarboxamido-3-(1,3-dimethoxyphenyl)indenone
2-ethylcarboxamidoindenone
2-ethylcarboxamido-3-hydroxyindenone
2-ethylcarboxamido-3-methylindenone
2-ethylcarboxamido-3-ethyl indenone
2-ethylcarboxamido-3-propylindenone
2-ethylcarboxamido-3-isopropylindenone
2-ethylcarboxamido-3-(3-chloropropyl)indenone
2-ethylcarboxamido-3-butylindenone
2-ethylcarboxamido-3-isobutylindenone
2-ethylcarboxamido-3-t-butylindenone
2-ethylcarboxamido-3-(3-methylbutyl)indenone
2-ethylcarboxamido-3-(1-ethylpropyl)indenone
2-ethylcarboxamido-3-hexylindenone
2-ethylcarboxamido-3-(4-methylpentyl)indenone
2-ethylcarboxamido-3-pentylindenone
2-ethylcarboxamido-3-ethenylindenone
2-ethylcarboxamido-3-(2-buten-1-yl)indenone
2-ethylcarboxamido-3-(3-buten-1-yl)indenone
2-ethylcarboxamido-3-ethynylindenone
2-ethylcarboxamido-3-(2-propynyl)indenone
2-ethylcarboxamido-3-(2-butynyl)indenone
2-ethylcarboxamido-3-cyclopropylindenone
2-ethylcarboxamido-3-cyclopentylindenone
2-ethylcarboxamido-3-cyclohexylindenone
2-ethylcarboxamido-3-(5-chloropentyl) indenone
2-ethylcarboxamido-3-phenylindenone
2-ethylcarboxamido-3-(1-chloro-2-methylbutyl)indenone
2-ethylcarboxamido-3-(1-bromo-2-methylbutyl)indenone
2-ethylcarboxamido-3-1-(iodo-2-methylbutyl)indenone
2-ethylcarboxamido-3-(1-chloro-2-methylpentyl)indenone
2-ethylcarboxamido-3-(1-bromo-2-ethylbutyl)indenone
2-ethylcarboxamido-3-(4-ethylphenyl) indenone
2-ethylcarboxamido-3-(2-ethylphenyl)indenone
2-ethylcarboxamido-3-(1,3-dimethoxyphenyl)indenone
2-propylcarboxamidoindenone
2-propylcarboxamido-3-hydroxyindenone
2-propylcarboxamido-3-methylindenone
2-propylcarboxamido-3-ethyl indenone
2-propylcarboxamido-3-propylindenone
2-propylcarboxamido-3-isopropylindenone
2-propylcarboxamido-3-(3-chloropropyl)indenone
2-propylcarboxamido-3-butylindenone
2-propylcarboxamido-3-isobutylindenone
2-propylcarboxamido-3-t-butylindenone
2-propylcarboxamido-3-(3-methylbutyl)indenone
2-propylcarboxamido-3-(1-ethylpropyl)indenone
2-propylcarboxamido-3-hexylindenone
2-propylcarboxamido-3-(4-methylpentyl)indenone
2-propylcarboxamido-3-pentylindenone
2-propylcarboxamido-3-ethenylindenone
2-propylcarboxamido-3-(2-buten-1-yl)indenone
2-propylcarboxamido-3-(3-buten-1-yl)indenone
2-propylcarboxamido-3-ethynylindenone
2-propylcarboxamido-3-(2-propynyl)indenone
2-propylcarboxamido-3-(2-butynyl)indenone
2-propylcarboxamido-3-cyclopropylindenone
2-propylcarboxamido-3-cyclopentylindenone
2-propylcarboxamido-3-phenylindenone
2-propylcarboxamido-3-(5-chloropentyl)indenone
2-propylcarboxamido-3-phenylindenone
2-propylcarboxamido-3-(1-chloro-2-methylbutyl)indenone
2-propylcarboxamido-3-(1-bromo-2-methylbutyl)indenone
2-propylcarboxamido-3-(1-iodo-2-methylbutyl)indenone
2-propylcarboxamido-3-(1-chloro-2-methylpentyl)indenone
2-propylcarboxamido-3-(1-bromo-2-ethylbutyl)indenone
2-propylcarboxamido-3-(4-ethylphenyl)indenone
2-propylcarboxamido-3-(2-ethylphenyl)indenone
2-propylcarboxamido-3-(1,3-dimethoxyphenyl)indenone
2-isopropylcarboxamidoindenone
2-isopropylcarboxamido-3-hydroxyindenone
2-isopropylcarboxamido-3-methylindenone
2-isopropylcarboxamido-3-ethylindenone
2-isopropylcarboxamido-3-propylindenone
2-isopropylcarboxamido-3-isopropylindenone
2-isopropylcarboxamido-3-(3-chloropropyl)indenone
2-isopropylcarboxamido-3-butylindenone
2-isopropylcarboxamido-3-isobutylindenone
2-isopropylcarboxamido-3-t-butylindenone
2-isopropylcarboxamido-3-(3-methylbutyl)indenone
2-isopropylcarboxamido-3-(1-ethylpropyl)indenone
2-isopropylcarboxamido-3-hexylindenone
2-isopropylcarboxamido-3-(4-methylpentyl)indenone
2-isopropylcarboxamido-3-pentylindenone
2-isopropylcarboxamido-3-ethenylindenone
2-isopropylcarboxamido-3-(2-buten-1-yl)indenone
2-isopropylcarboxamido-3-(3-buten-1-yl)indenone
2-isopropylcarboxamido-3-ethynylindenone
2-isopropylcarboxamido-3-(2-propynyl)indenone
2-isopropylcarboxamido-3-(2-butynyl)indenone
2-isopropylcarboxamido-3-cyclopropylindenone 2-isopropylcarboxamido-3-cyclopentylindenone
2-isopropylcarboxamido-3-phenylindenone
2-isopropylcarboxamido-3-cyclohexylindenone
2-isopropylcarboxamido-3-(5-chloropentyl)indenone
2-isopropylcarboxamido-3-phenylindenone
2-isopropylcarboxamido-3-(1-chloro-2-methylbutyl) indenone
2-isopropylcarboxamido-3-(1-bromo-2-methylbutyl) indenone
2-isopropylcarboxamido-3-(1-iodo-2-methylbutyl) indenone
2-isopropylcarboxamido-3- (-chloro-2-methylpentyl) indenone
2-isopropylcarboxamido-3-(1-bromo-2-ethylbutyl) indenone
2-isopropylcarboxamido-3-(4-ethylphenyl) indenone
2-isopropylcarboxamido-3-(2-ethylphenyl) indenone
2-isopropylcarboxamido-3-(1,3-dimethoxyphenyl) indenone
2-butylcarboxamidoindenone
2-butylcarboxamido-3-hydroxyindenone
2-butylcarboxamido-3-methylindenone
2-butylcarboxamido-3-ethyl indenone
2-butylcarboxamido-3-propylindenone
2-butylcarboxamido-3-isopropylindenone
2-butylcarboxamido-3-(2-chloropropyl)indenone
2-butylcarboxamido-3-butylindenone
2-butylcarboxamido-3-isobutylindenone
2-butylcarboxamido-3-t-butylindenone
2-butylcarboxamido-3-(3-methylbutyl)indenone
2-butylcarboxamido-3-(1-ethylpropyl)indenone
2-butylcarboxamido-3-hexylindenone
2-butylcarboxamido-3-(4-methylpentyl)indenone
2-butylcarboxamido-3-pentylindenone
2-butylcarboxamido-3-ethenylindenone
2-butylcarboxamido-3-(2-buten-1-yl)indenone
2-butylcarboxamido-3-(3-buten-1-yl)indenone
2-butylcarboxamido-3-ethynylindenone
2-butylcarboxamido-3-(2-propynyl)indenone
2-butylcarboxamido-3-(2-butynyl)indenone
2-butylcarboxamido-3-cyclopropylindenone
2-butylcarboxamido-3-cyclopentylindenone
2-butylcarboxamido-3-cyclohexylindenone
2-butylcarboxamido-3-(5-chloropentyl)indenone
2-butylcarboxamido-3-phenylindenone
2-butylcarboxamido-3-(1-chloro-2-methylbutyl)indenone
2-butylcarboxamido-3-(1-bromo-2-methylbutyl) indenone
2-butylcarboxamido-3-(1-iodo-2-methylbutyl)indenone
2-butylcarboxamido-3-(1-chloro-2-methylpentyl) indenone
2-butylcarboxamido-3-(1-bromo-2-ethylbutyl)indenone
2-butylcarboxamido-3-(4-ethylphenyl) indenone
2-butylcarboxamido-3-(4-ethylphenyl)indenone
2-butylcarboxamido-3-(2-ethylphenyl )indenone
2-butylcarboxamido-3-(1,3-dimethoxyphenyl)indenone
2-butylcarboxamido-5,6-dihydroxyindenone
2-butylcarboxamido-3,5,6-trihydroxyindenone
2-butylcarboxamido-5,6-dihydroxy-3-methylindenone
2-butylcarboxamido-5,6-dihydroxy-3-ethylindenone
2-butylcarboxamido-5,6-dihydroxy-3-propylindenone
2-butylcarboxamido-5,6-dihydroxy-3-isopropylindenone
2-butylcarboxamido-5,6-dihydroxy-3-(3-chloropropyl) indenone
2-butylcarboxamido-5,6-dihydroxy-3-butylindenone
2-butylcarboxamido-5,6-dihydroxy-3-isobutylindenone
2-butylcarboxamido-5,6-dihydroxy-3-t-butylindenone
2-butylcarboxamido-5,6-dihydroxy-3-(3-methylbutyl) indenone
2-butylcarboxamido-5,6-dihydroxy-3-(1-ethylpropyl) indenone
2-butylcarboxamido-5,6-dihydroxy-3-hexylindenone
2-butylcarboxamido-5,6-dihydroxy-3-(4-methylpentyl) indenone
2-butylcarboxamido-5,6-dihydroxy-3-pentylindenone
2-butylcarboxamido-5,6-dihydroxy-3-ethenylindenone
2-butylcarboxamido-5,6-dihydroxy-3-(2-buten-1-yl) indenone
2-butylcarboxamido-5,6-dihydroxy-3-(3-buten-1-yl) indenone
2-butylcarboxamido-5,6-dihydroxy-3-ethynylindenone
2-butylcarboxamido-5,6-dihydroxy-3-(2-propynyl) indenone
2-butylcarboxamido-5,6-dihydroxy-3-(2-butynyl) indenone
2-butylcarboxamido-5,6-dihydroxy-3-cyclopropylindenone
2-butylcarboxamido-5,6-dihydroxy-3-cyclopentylindenone
2-butylcarboxamido-5,6-dimethoxyindenone
2-butylcarboxamido-5,6-dimethoxy-3-hydroxyindenone
2-butylcarboxamido-5,6-dimethoxy-3-methylindenone
2-butylcarboxamido-5,6-dimethoxy-3-ethylindenone
2-butylcarboxamido-5,6-dimethoxy-3-propylindenone
2-butylcarboxamido-5,6-dimethoxy-3-isopropylindenone
2-butylcarboxamido-5,6-dimethoxy-3-(3-chloropropyl) indenone
2-butylcarboxamido-5,6-dimethoxy-3-butylindenone
2-butylcarboxamido-5,6-dimethoxy-3-isobutylindenone
2-butylcarboxamido-5,6-dimethoxy-3-t-butylindenone
2-butylcarboxamido-5,6-dimethoxy-3-(3-methylbutyl) indenone
2-butylcarboxamido-5,6-dimethoxy-3-ethylpropylindenone
2-butylcarboxamido-5,6-dimethoxy-3-hexylindenone
2-butylcarboxamido-5,6-dimethoxy-3-(4-methylpentyl) indenone
2-butylcarboxamido-5,6-dimethoxy-3-pentylindenone
2-butylcarboxamido-5,6-dimethoxy-3-ethenylindenone
2-butylcarboxamido-5,6-dimethoxy-3-(2-buten-1-yl) indenone
2-butylcarboxamido-5,6-dimethoxy-3-(3-buten-1-yl) indenone
2-butylcarboxamido-5,6-dimethoxy-3-ethynylindenone
2-butylcarboxamido-5,6-dimethoxy-3-(2-propynyl) indenone
2-butylcarboxamido-5,6-dimethoxy-3-(2-butynyl) indenone
2-butylcarboxamido-5,6-dimethoxy-3-cyclopropylindenone
2-butylcarboxamido-5,6-dimethoxy-3-cyclopentylindenone The preferred treatment methods of this invention employ the compounds of formula I, wherein $R_1$ and $R_2$ independently are hydrogen, hydroxy, $C_1$–$C_4$ alkyl or $C_1$–$C_4$ alkoxy; $R_3$ is $C_1$–$C_6$ alkyl, $C_1$–$C_6$ alkoxy, $C_2$–$C_6$ alkenyl, $C_2$–$C_6$ alkynyl, $C_4$–$C_6$ cycloalkyl, or halo($C_1$–$C_6$ alkyl); and $R_4$ is hydrogen or $C_1$–$C_4$ alkyl.

The most preferred treatment methods of this invention employ the compounds of formula I, wherein $R_1$, $R_2$ and $R_4$ are hydrogen and $R_3$ is methyl, ethyl, n-propyl, 3-chloropropyl, isopropyl, n-butyl, n-pentyl or phenyl.

The preferred compounds of this invention are the compounds of formula Ia where $R_1$ and $R_2$ are each H or $C_1$–$C_4$ alkyl, $R_3$ is $C_1$–$C_6$ alkyl, $C_2$–$C_6$ alkenyl, or $C_1$–$C_6$ alkoxy; and $R_4$ is hydrogen or $C_1$–$C_4$ alkyl; provided that:

when $R_1$ and $R_2$ are both hydrogen, $R_3$ is other than $C_1$–$C_4$ alkyl, halo($C_1$–$C_6$ alkyl), cyclopropyl or phenyl.

A most preferred compound of this invention is 2-carboxamido-3-pentylindenone.

Unless otherwise described herein, the following definitions are used in this document: The term "halo" includes fluoro, chloro, bromo and iodo. "$C_1$–$C_4$ alkyl and $C_1$–$C_6$ alkyl" represent a straight or branched chain alkyl group having one to four or six carbon atoms, respectively, such as methyl, ethyl, propyl, isopropyl, butyl, isobutyl, t-butyl, pentyl, 3-methylbutyl, 1-ethylpropyl, hexyl or 4-methylpentyl. The terms "$C_1$–$C_4$ alkoxy" and "$C_1$–$C_6$ alkoxy" represent, respectively, any $C_1$–$C_4$ alkyl or $C_1$–$C_6$ alkyl group covalently bonded to the parent moiety by an —O— linkage. "$C_2$–$C_6$ alkenyl", as used herein, represents a straight chain or branched, unsaturated aliphatic chain having from two to six carbon atoms with one double bond. Typical $C_2$–$C_6$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 1-butenyl, 2-pentenyl, and the like. "$C_2$–$C_6$ alkynyl" as used herein, represents a straight chain or branched unsaturated aliphatic chain having from two to six carbon atoms with one triple bond. Typical $C_2$–$C_6$ alkynyl groups include ethynyl, 2-propynyl, 2-butynyl and iso-2-butynyl, 1-pentynyl, 2-pentynyl, 1-hexynyl, 2-hexynyl, and the like. "$C_3$–$C_6$ cycloalkyl" is cyclopropyl, cyclobutyl, cyclopentyl or cyclohexyl. The term "halo($C_1$–$C_6$ alkyl)" represents a straight or branched chain alkyl group having from one to six carbon atoms with a halogen atom bonded thereto. Typical halo($C_1$–$C_6$ alkyl) groups include 3-chlorobutyl, 4-chlorobutyl, 5-chlorobutyl, 3-iodobutyl, 4-iodobutyl, 5-iodobutyl, 3-fluorobutyl, 4-fluorobutyl, 5-fluorobutyl and the like. The term "substituted phenyl" refers to a phenyl group containing one or two substituents on the phenyl ring that will afford a stable structure independently selected from halo, hydroxy, $C_1$–$C_4$ alkyl, halo($C_1$–$C_6$ alkyl) or $C_1$–$C_4$ alkoxy.

This invention includes a salt of a compound defined by formula I. Particular compounds of this invention possess at least one basic functional group to react with any of a number of inorganic and organic acids to form a salt. All of these forms are within the scope of this invention.

Acids commonly employed to form pharmaceutically acceptable acid addition salts include inorganic acids such as hydrochloric, hydrobromic, hydroiodic, sulfuric and phosphoric acid, as well as organic acids such as paratoluenesulfonic, methanesulfonic, oxalic, parabromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, butyne-1,4-dioate, hexyne-1,6-dioate, benzoate, chlorobenzoate, methylbenzoate, dinitrobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycollate, maleate, tartrate, methanesulfonate, propanesulfonate, naphthalene-1-sulfonate, naphthalene-2-sulfonate, mandelate and the like salts.

It is recognized that this invention is not limited to any particular stereoisomer but includes all possible individual isomers and mixtures thereof.

The compounds of the present invention are known to form solvates with appropriate solvents. Preferred solvents for the preparation of solvate forms include water, alcohols, tetrahydrofuran (THF), DMF, and DMSO. Preferred alcohols are methanol and ethanol. Other appropriate solvents may be selected based on the size of the solvent molecule. Small solvent molecules are preferred to facilitate the corresponding solvate formation. The solvate is typically formed in the course of recrystallization or in the course of salt formation. One useful reference concerning solvates is P. Sykes, *A Guidebook to Mechanism in Organic Chemistry*, 6, 56, John Wiley & Sons (1986). The term "solvate" as used herein includes hydrate forms such as monohydrate and dihydrates.

The desired products from the above reactions can be isolated by conventional means, and preferably by chromatography. Column chromatography is a preferred method and high pressure column chromatography over silica gel offers the most efficient way of purifying the final products. Alternatively, crystallization of the free base or salts may be employed to purify the desired final product.

The preparation of the indenone amide compounds of this invention can be effected starting from known compounds according to methods which are known and which are familiar to any person skilled in the art.

One process for preparing many of the compounds of formula I is outlined in Scheme I. The ylidenemalononitrile compounds III can be obtained by coupling a substituted or unsubstituted carbonyl compound II, for example, chlorobutyrophenone, with malononitrile. The coupling reactions can be carried out according to methods which are known per se in the art. For example, according to the general procedure of Mowery, *J. Am. Chem. Soc.*, 67, 1050 (1945), the aldehyde, malononitrile, an ammonium salt (such as, ammonium acetate), acetic acid, and benzene can be stirred at a temperature between 0° C. and reflux. The resultant ylidenemalononitriles III can then be purified by standard methods.

Cyclization of these compounds to the indenone amide compounds IV can be performed by those methods disclosed in the art. For example, the general method of Campaigne et al., *J. Org. Chem.*, 27, 4428 (1963) and *J. Heterocyclic Chem.*, 14, 1337 (1977), by treatment with an acid, for example, sulfuric acid. The acid may be used either neat or diluted in an appropriate inert solvent at a temperature between −5° C. and 100° C. Other acids could be used including hydrochloric acid, trifluoroacetic acid, polyphosphoric acid, and the like. The resulting indenone amide compounds IV can be purified by chromatography, crystallization, and/or distillation techniques.

Scheme I

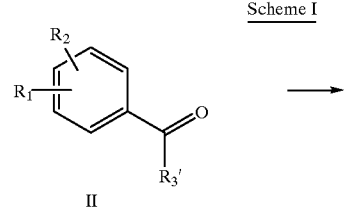

II

-continued

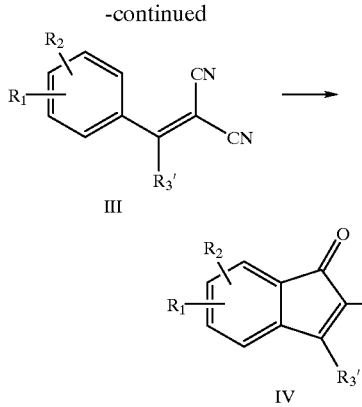

where $R_1$ and $R_2$ are as defined for formula I, and $R_3'$ is hydrogen, $C_1$–$C_6$ alkyl, $C_2$–$C_6$ alkenyl, $C_2$–$C_6$ alkynyl, $C_3$–$C_6$ cycloalkyl, halo($C_1$–$C_6$ alkyl) or unsubstituted or substituted phenyl.

The preparation of the substituted analogs of carbonyl compound II of this invention can be effected starting from known compounds according to methods which are known and which are familiar to any person skilled in the art.

The carbonyl compounds of formula II may also be prepared by a Friedel-Crafts acylation of the substituted benzene V with an appropriate acyl halide or carboxylic acid derivative in the presence or absence of a Lewis acid catalyst, for example, aluminum chloride (Scheme II). Other Lewis acids could be used including aluminum tribromide, stannic chloride, ferric chloride, zinc chloride, boron trifluoride, and the like. Proton acids, such as trifluoroacetic acid, can be used when the reagent is a carboxylic acid. Other proton acids could be used including hydrochloric acid, sulfuric acid, and the like. See: J. March, *Advanced Organic Chemistry, Reactions. Mechanisms. and Structure*, 3rd Edition, John Wiley & Sons, 484 (1985). The resulting carbonyl compounds of formula II can be purified by chromatography, crystallization, and/or distillation techniques. Regioisomeric products of formula II can be separated by standard methods, such as, crystallization or chromatography.

Scheme II

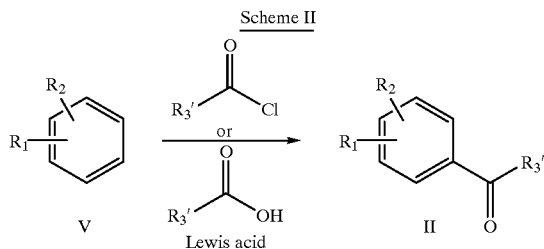

where $R_1$, $R_2$ and $R_3'$ are as defined for Scheme I.

Alternatively, the carbonyl compounds II can be prepared from the corresponding carboxylic acids VI (Scheme III). The preparation of the substituted analogs of carboxylic acids VI of this invention can be effected starting from known compounds according to methods which are known and which are familiar to any person skilled in the art. The carboxylic acid VI can be converted to the carbonyl compounds II by treatment with the appropriate organolithium reagent according to the procedure of Rubottom and Kim, *J. Org. Chem.*, 48, 1550 (1983). The carboxylic acid VI can also be converted to the carbonyl compounds II by conversion to the acyl halide VII under standard conditions, for example, by reaction with thionyl chloride or oxalyl chloride. See: J. March, *Advanced Organic Chemistry, Reactions, Mechanisms, and Structure*. 3rd Edition, John Wiley & Sons, 388 (1985). The resultant acyl halide VII can then be condensed with an organometallic compound, such as, a lithium dialkylcopper reagent or organocadmium to give the carbonyl compounds II.

Scheme III

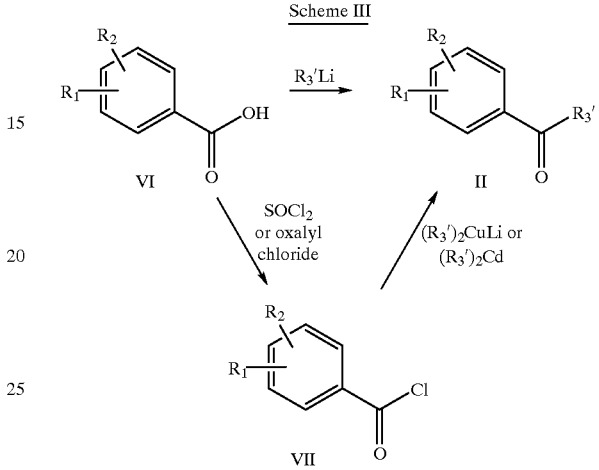

where $R_1$ and $R_2$ are as defined for formula I, and $R_3'$ is $C_1$–$C_6$ alkyl, $C_2$–$C_6$ alkenyl, $C_2$–$C_6$ alkynyl, $C_3$–$C_6$ cycloalkyl, halo($C_1$–$C_6$ alkyl) or unsubstituted or substituted phenyl.

The indenonecarboxamides of formula I can be prepared by first preparing the ester XI according to the method of Babin and Dunoques, *Tet. Lett.*, 25, 4389–4392 (1984) (Scheme IV). The preparation of the substituted analogs of carboxylic acids VIII of this invention can be effected starting from known compounds according to methods which are known and which are familiar to any person skilled in the art. The carboxylic acid VIII can be treated with thionyl chloride in an inert solvent, such as methylene chloride, at an appropriate temperature between 0° C. and 40° C. The resulting acid chloride IX can then be condensed with an appropriate phosphorane, such as, (carboethoxymethylene)triphenyl-phosphorane in an inert solvent, such as toluene, at an appropriate temperature between 0° C. and 40° C. Other phosporanes, such as, (carbomethoxymethylene)triphenyl-phosphorane, (carbo-t-butoxymethylene)triphenylphosphorane, (carbobenzyloxymethylene)triphenylphosphorane, and the like, can be used. The resulting phosphorane X can be isolated and purified or directly converted to the indenone XI by heating X in an inert solvent, such as toluene, at an appropriate temperature between 40° C. and 120° C. via the loss of triphenylphosphine oxide.

Scheme IV

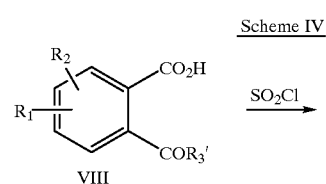

-continued

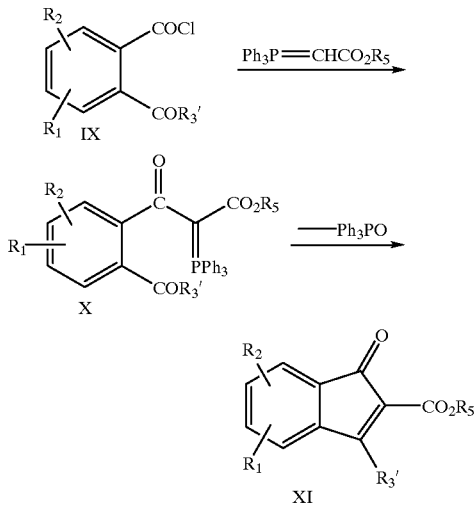

where $R_1$, $R_2$ and $R_3'$ are as defined for Scheme I; and $R_5$ is, for example, $C_1$–$C_4$ alkyl or benzyl.

The ester XI can then be condensed with an appropriate amine to give the corresponding amide Ib in a manner similar to that described in U.S. Pat. No. 3,413,308 which is incorporated by reference herein (Scheme V). The reaction is carried out in the presence of an inert organic solvent at an appropriate temperature.

Scheme V

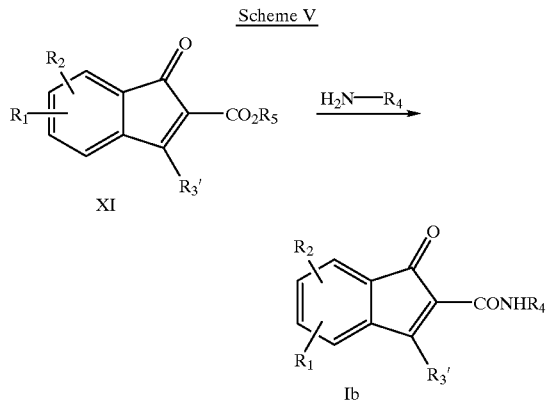

where $R_1$, $R_2$, $R_3'$ and $R_4$ are as defined in Formula I, and $R_5$ is, for example, $C_1$–$C_4$ alkyl or benzyl.

The free acid XIII can also be prepared by saponification of ester XI under standard conditions. For example, the ester XI can be saponified with sodium hydroxide in aqueous methanol at an appropriate temperature between –20° C. and 40° C. If $R_5$ is a hydrogen labile group, such as benzyl, $R_5$ can be removed by catalytic hydrogenation with, for example, palladium on carbon at an appropriate temperature between 25° C. and 100° C. in an inert solvent such as tetrahydrofuran or ethanol under between 1 to 100 atmospheres of hydrogen to afford the free acid XIII (Scheme VI).

Scheme VI

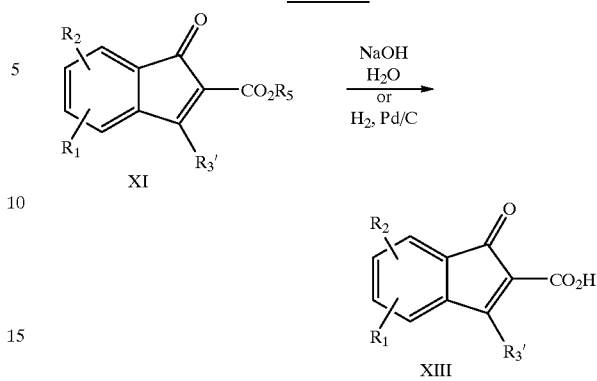

where $R_1$, $R_2$, $R_3'$ and $R_5$ are as defined for Scheme IV.

The free acid can then be converted to the acid chloride XIV, for example by reaction with thionyl chloride in an inert solvent, such as methylene chloride, at an appropriate temperature between –20° C. and 40° C., or converted to an activated ester XV, for example, with dicyclohexylcarbodiimide in an inert solvent, such as tetrahydrofuran or acetonitrile, at an appropriate temperature between –20° C. and 40° C. (Scheme VII). The acid chloride or activated ester can then be coupled with amine, $R_4NH_2$, in an inert solvent, such as methylene chloride, at an appropriate temperature between –20° C. and 40° C. to afford the corresponding amide I.

Scheme VII

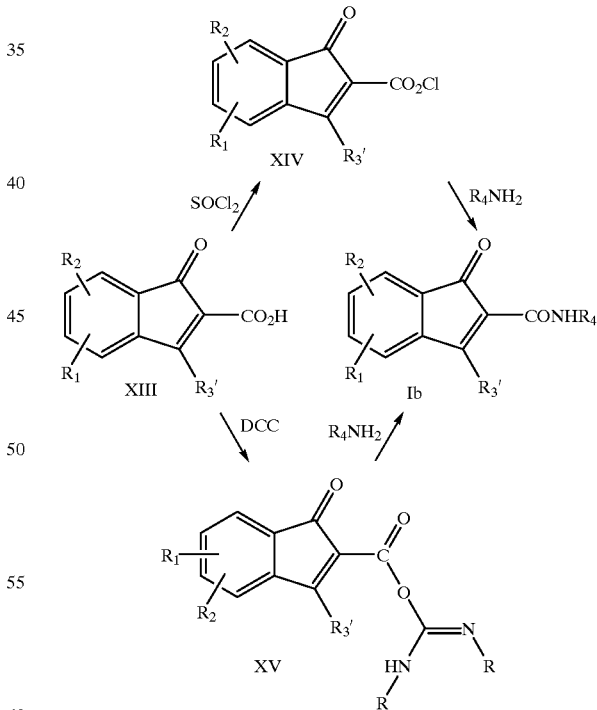

where R is cyclohexyl and $R_1$, $R_2$, $R_3$, and $R_4$ are as defined in formula I.

The 3-alkoxy derivatives XXI, that are available via the method of Babin and Dunoques, Tet Lett., 24, 3071–3074, (1983) can be processed in a like manner to that of amide I. The preparation of the substituted analogs of the dicarboxylic acid compound XVI of this invention can be effected starting from known compounds according to methods which are known and which are familiar to any person skilled in the art. The corresponding anhydride XVII can be obtained by treatment of dicarboxylic acid XVI with acetic anhydride in a manner similar to that of Nicolet and Bender as described in *Organic Syntheses*, 1, 410 (1941) which is incorporated by reference herein (Scheme VIII). The reaction is carried out in the presence or absence of an inert organic solvent at an appropriate temperature. The anhydride XVII can be reacted with an appropriate alcohol in a manner similar to that of Kenyon as described in *Organic Syntheses*, 1, 418 (1941), to afford the acid/ester derivative XVIII. The reaction is carried out in the presence or absence of an inert organic solvent at an appropriate temperature. The resulting acid/ester compounds of formula XVIII can be purified by chromatography, crystallization, and/or distillation techniques. Regioisomeric products of formula XVIII can be separated by standard methods, such as, crystallization or chromatography. The acid/ester derivative XVIII can be converted to the indenone ester derivative XXI by the method of Babin and Dunoques, *Tet. Lett.*, 24, 3071–3074 (1983) which is incorporated by reference herein. The acid/ester derivative XVIII can be treated with thionyl chloride in an inert solvent, such as methylene chloride, at an appropriate temperature between 0° C. and 40° C. The resulting acid chloride XIX can then be condensed with an appropriate phosphorane, such as, (carboethoxymethylene)triphenylphosphorane in an inert solvent, such as toluene, at an appropriate temperature between 0° C. and 40° C. Other phosphoranes, such as, (carbomethoxymethylene)triphenylphosphorane, (carbo-t-butoxymethylene)triphenylphosphorane, (carbobenzyloxymethylene)triphenylphosphorane, and the like, can be used. The resulting phosphorane XX can be isolated and purified or directly converted to the indenone XXI by heating XX in an inert solvent, such as toluene, at an appropriate temperature between 40° C. and 120° C. via the loss of triphenylphosphine oxide.

Scheme VIII

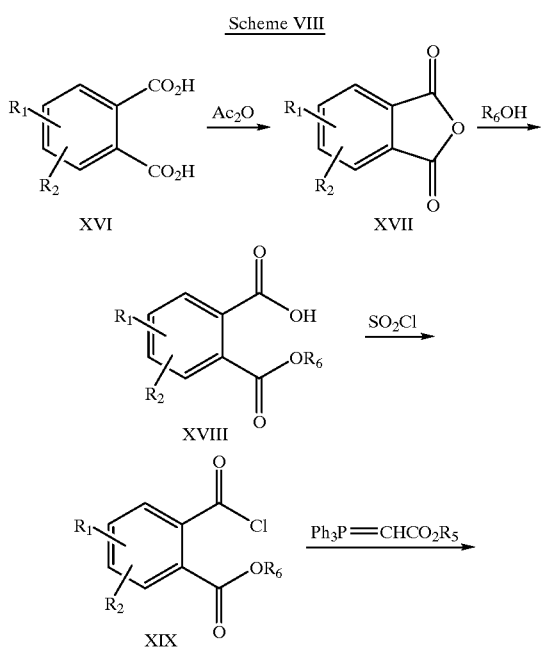

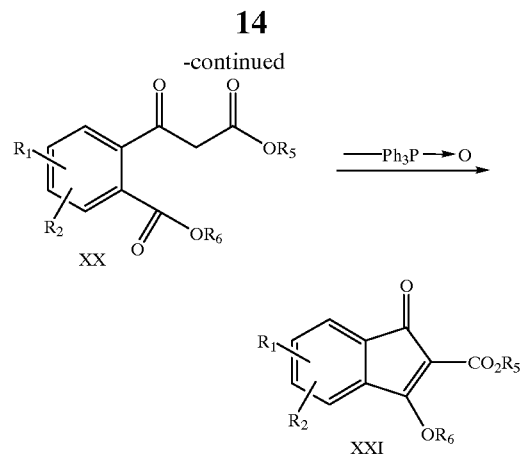

where $R_1$, $R_2$ and $R_3$ are as defined for formula I, $R_5$ is, for example, $C_1$–$C_4$ alkyl or benzyl, and $R_6$ is, for example, $C_1$–$C_6$ alkyl or benzyl.

The ester XXI can then be condensed with an appropriate amine to give the corresponding amide XXII (Scheme IX) in a manner similar to that described in U.S. Pat. No. 3,413,308 which is incorporated by reference herein, and as described above for the conversion of XI to I (Scheme V). The reaction is carried out in the presence of an inert organic solvent at an appropriate temperature.

Scheme IX

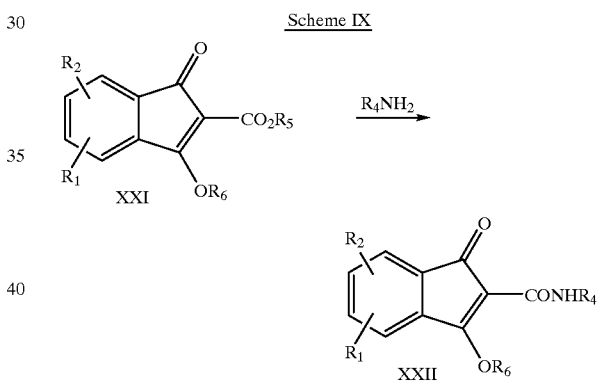

wherein $R_1$, $R_2$, $R_4$, $R_5$ and $R_6$ are as defined in Scheme VIII.

Alternatively, the free acid XXIII can also be prepared by saponification of ester XXI under standard conditions. For example, the ester XXI can be saponified with potassium carbonate in aqueous methanol at an appropriate temperature between −20° C. and 40° C. If $R_5$ is a hydrogen labile group, such as benzyl, $R_5$ can be removed by catalytic hydrogenation with, for example, with palladium on carbon at an appropriate temperature between 25° C. and 100° C. in an inert solvent such as tetrahydrofuran or ethanol under between 1 to 100 atmospheres of hydrogen to afford the free acid XXIII (Scheme X).

Scheme X

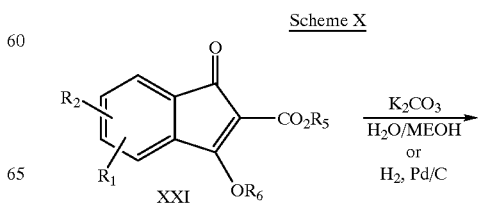

-continued

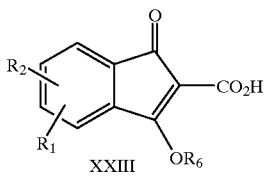

wherein $R_1$, $R_2$, $R_3$, $R_5$ and $R_6$ are as defined in Scheme VIII.

The free acid can then be converted to the acid chloride XXIV, for example by reaction with thionyl chloride in an inert solvent, such as methylene chloride, at an appropriate temperature between −20° C. and 40° C., or to the activated ester XXV, for example with dicyclohexylcarbodiimide in an inert solvent, such as tetrahydrofuran or acetonitrile, at an appropriate temperature between −20° C. and 40° C. (Scheme XI). The acid chloride or activated ester can then be coupled with an amine in an inert solvent, such as methylene chloride, at an appropriate temperature between −20° C. and 40° C. to afford the corresponding amide XXII.

Scheme XI

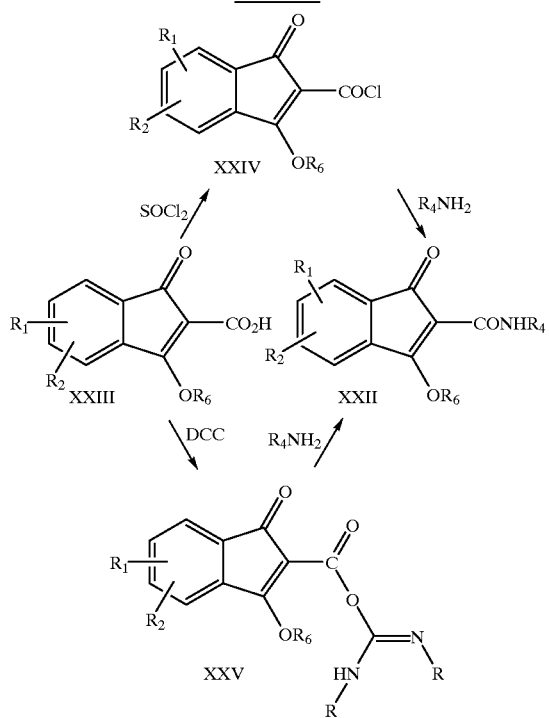

wherein R is cyclohexyl and $R_1$, $R_2$, $R_4$, $R_5$ and $R_6$ are as defined in Scheme VIII.

The following preparations are provided merely to further illustrate the invention. The scope of the invention is not construed as merely consisting of the following preparations.

Preparation of Ylidenemalononitriles (II)

The general method of Mowery, *J. Am. Chem, Soc.*, 67, 1050 (1945) as modified by Campaigne et al., *J. Org. Chem.*, 27, 4428 (1963) can be used. The carbonyl compound of formula II (0.5 mol), malononitrile (0.6 mol), anhydrous ammonium acetate (4.0–32.0 g, 0.05–0.4 mol), glacial acetic acid (12 ml), and benzene (400 ml) can be heated at reflux for 4–12 hours until the amount of water in the Dean-Stark water trap remains constant. The resulting benzene solution is cooled to room temperature, washed with water, dried over sodium sulfate, filtered, and concentrated to afford a dinitrile as an oil or solid.

Cyclization to Indenone Amides (III)

The general method of Campaigne et al., *J. Org. Chem.* 27, 4428 (1963), and *J. Heterocyclic Chem.* 14, 1337 (1977), can be used. The ylidenemalonitrile (0.01 mol) is dissolved in 20 ml concentrated sulfuric acid and heated at 50–55° C. for 0.5–8 hours, then poured over 200 grams of ice. The resultant precipitate is collected by filtration and purified by chromatography and/or crystallization.

The compounds of formula I are potent effective inhibitors of leukocyte adherence to vascular endothelial cells. As such, they are useful in treating conditions associated with excessive or unregulated leukocyte accumulation, such as, but not limited to, the following inflammatory diseases and other conditions: rheumatoid arthritis, asthma, psoriasis, stroke, Alzheimer's disease, respiratory distress syndrome, reperfusion injury, ischemia, ulcerative colitis, vasculitis, atherosclerosis, inflammatory bowel disease, and tumor metastases.

Representative compounds of the formula I were evaluated and found to effectively inhibit neutrophil adhesion to keyhole limpet hemocyanin (KLH) and to inhibit human neutrophils from adhering to ICAM-1 bearing endothelial cells. These test systems are described below. Also, it is known that excess accumulation of leukocytes may lead to release of toxic oxygen radicals that potentiate tissue damage. Accordingly, representative compounds of the formula I were evaluated and found to effectively inhibit adhesion dependent oxidant production in the Inhibition of Adhesion-Dependent Oxidant Production test system described below.

Isolation of Human Neutrophils

Venous blood was drawn from healthy donors into citrate-phosphate dextrose anti-coagulant. Five ml of the collected blood were mixed with 1.5 ml 6% dextran in 0.87% NaCl solution (Macrodex®) and incubated at 37° C. for 25–35 minutes until the erythrocytes agglutinated and settled to the bottom of the tube. The supernatant fluid was removed and centrifuged at room temperature for 5 minutes at 300 g. The resulting cell pellet was resuspended in a volume of Dulbecco's phosphate buffered saline (PBS) containing 0.2% glucose that was equal to the original blood volume. In 10 ml portions, the suspension was layered over 5 ml of Ficoll-Paque® and centrifuged at room temperature for 20 minutes at 675 g. All of the supernatant fluid and the resulting mononuclear cell layer were carefully removed and discarded. The pellet was resuspended as above, the cell density determined with a Cell-Dyne 1600 and the suspension centrifuged at 300 g for 5 minutes. The differential white blood cell (WBC) count was >90% granulocytes. After discarding the supernatant fluid, the cell pellet was resuspended as above at 1 million granulocytes/ml and used promptly in the assay.

Inhibition of Adhesion-Dependent Oxidant Production

Compounds were evaluated for their ability to inhibit hydrogen peroxide produced by neutrophils after the cells had been stimulated with formyl-L-methionyl-L-leucyl-L-phenylalanine (fMLP) to adhere and spread on a keyhole limpet hemocyanin (KLH)-coated surface. The amount of peroxide produced was measured by reacting it enzymatically with the fluorescent substrate, scopoletin. The reaction was carried out in 96-well plates using a protocol very similar to that reported by Shappell et al., *J. Immunol.*, 144, 2702–2711 (1990). Tissue culture plates (Linbro/ICN Flow) were prepared by filling each well with 250 μl of a filtered solution of 0.5 mg/ml KLH in carbonate-bicarbonate buffer containing 0.02% sodium azide. Plates were tightly sealed, incubated at 37° C. for 2–18 hours and then stored at 4° C. for up to 6 weeks. Just prior to being used, plates were washed twice with 250 μl Dulbecco's PBS per well and patted dry. All reagents were dissolved in a Krebs-Ringer-Phosphate (KRP) buffer containing 0.1% glucose, pH 7.35, 145 mM NaCl, 4.86 mM KCl, 0.54 mM $CaCl_2$, 1.22 mM $MgSO_4$, and 5.77 mM $Na_2HPO_4$. Compounds were initially dissolved in dimethylsulfoxide (DMSO) at 50 mM and stored at 4° C. until used. Appropriate dilutions were made with the KRP buffer to yield working solutions containing 0.2% DMSO. To start the reaction, wells were initially filled with 100 μl of buffer containing 0.2% DMSO or appropriate stock inhibitor solution. Next, 25 μl of fluorescent indicator mixture containing 5.6 mM sodium azide, 136 μM scopoletin and 28.8 μg/ml of horseradish peroxidase was added to each well. Then 25 μl of 240 nM fMLP in PBS was dispensed into the wells. The reaction was started by adding 50 μl of cell suspension ($1\times10^6$ cells per ml). All experiments were carried out at 37° C. Spontaneous oxidation of scopoletin was monitored by observing the loss of fluorescence in wells to which no cells had been added. Fluorescence readings were made with either a Millipore Cytofluor 2350 or PerSeptive Biosystems Cytofluor II using an excitation wavelength of 360 nm and an emission wavelength of 460 nm. Inhibition concentration studies were carried out by testing five, 3-fold dilutions of each compound. After a lag period of 15–30 minutes, cells stimulated in the absence of any inhibitor began to produce $H_2O_2$ and the fluorescence decreased rapidly for the next 30–45 minutes. The time points that bracketed the steepest drop in fluorescence of these positive control wells were used to determine the extent of reaction in all wells. The fluorescence decrease (f.d.) during this time period at all compound concentrations was measured and the percent inhibition determined with the following formula:

$$100\times \frac{\text{(f.d. of positive control} - \text{f.d. of compound-treated cells)}}{\text{(f.d. of positive control} - \text{f.d. of no cells control)}}$$

The $IC_{50}$ value was calculated assuming a linear relationship between percent inhibition and compound concentration in the region between 25% and 75% inhibition.

Inhibition of neutrophil adhesion.

Evaluation of the effects of compounds on CD11b-mediated adhesion was carried out using 96-well plates in a manner similar to that used in determining effects on adhesion-dependent oxidant production. The protocol was an adaptation from Shappell et al., *J. Immunol.*, 144, 2702–2711 (1990). Plates were coated with KLH as described previously but washed twice with PBS containing 3% low-endotoxin bovine serum albumin (BSA). Compounds were dissolved in DMSO and appropriate dilutions made with Hank's Balanced Salt Solution (HBSS) without $Ca^{++}$ and $Mg^{++}$. Initially 100 μl of the working compound solution was added to the wells. Then 25 μl of HBSS containing 0.8% BSA was dispensed in the wells. Next 50 μl of a neutrophil suspension ($1\times10^6$ cells/ml) was added. After 10 minutes of incubation, 25 μl of a solution containing 800 nM fMLP, 10 mM $CaCl_2$, and 6.5 mM $MgSO_4$ was put into the wells and the plates incubated at room temperature for 30–45 minutes The reaction fluid was then decanted and the wells were washed twice with HBSS containing 0.1 % BSA and the plates patted dry. The number of adherent neutrophils was measured indirectly by lysing the cells and determining the amount of myeloperoxidase liberated. To do this, 200 μl of o-phenylenediamine dihydrochloride (0.5 mg/ml) in phosphate-citrate buffer (50 mM) with 0.03% sodium perborate and 0.1% Triton-X100 was added per well. After 5 minutes, the optical density (OD) at 490 nm of each well was measured and the number of adherent cells determined from a standard curve made by measuring the absorbance of wells that had been filled with 2,500 to 50,000 neutrophils. The effect of each concentration of compound was assessed by comparison of the number of adherent cells in compound-treated wells with those in the positive control wells. $IC_{50}$ values were calculated assuming a linear relationship between percent inhibition and compound concentration in the region between 25% and 75% inhibition.

HUMAN NEUTROPHIL/ECV304 BINDING ASSAY

This assay measures the ability of compounds to inhibit fMLP-stimulated human neutrophils from adhering to the ICAM-1 expressing endothelial cell line ECV304. Bound neutrophils are quantified by their myeloperoxidase activities. ECV304 cells from the American Type Culture Collection (ATCC) were grown to confluency, after a 1:9 split, on Costar 96-well tissue culture plates (catalogue #3596). The cells were then stimulated with 10 μg/ml lipopolysaccharide (LPS) (Sigma catalogue L6016) overnight at 37° C. The plates were washed twice with PBS, and 105 μl of 2% fetal bovine serum in M199 media (Gibco BRL catalogue #11153–020) was then added to each well.

Blood was drawn into citrate-phosphate-dextrose anticoagulant (Sigma catalog #C-7165, 1.4 ml /10 ml blood) from donors free of anti-inflammatory drugs for the preceding 48 hours. Five ml of blood was layered over 3 ml Mono-Poly Resolving Medium (ICN, catalogue # 1698049) and centrifuged at 300x g for 30 minutes. The band containing polymorphonuclearleukocytes (PMN) was washed twice with PBS free of calcium and magnesium, and the cells resuspended in calcium and magnesium free Hank's balanced salt solution containing 0.1% BSA. Cell counts were performed using a Cell-Dyne 1600. PMN cell density was adjusted to 5 million/ml and used promptly in the assay.

Serial dilutions of test compounds were added to the wells followed by 50 μl of PMN suspension (250,000/well). Anti-CD18 MAb (5 μg/ml) was included as a control inhibitor. After 10 minutes, fMLP was added (final concentration 0.1 uM). The final assay volume was 200 μl per well. The plates were incubated at room temperature for 45 minutes. Plates were then washed with Hank's balanced salt solution containing 0.1% BSA. In testing for myeloperoxidase activity, 200 μl phosphate-citrate buffer containing sodium perborate (Sigma #P-4922), 1% Triton X-100 and o-phenylenediamine dihydrochloride (Sigma #P8412) (0.2 mg/ml) was added to each well. Plates were incubated at room temperature for 5 minutes and the reaction was stopped with the addition of 50 μl 4N sulfuric acid. Plates were read at 490 nm on a Bio-Tek Instruments micro-plate reader. Optical density (OD) values of specifically bound neutrophils were normalized by deducting the background OD of bound neutrophils that had not been stimulated by fMLP. The percent inhibition was defined as the ratio of the decrease in OD of compound-treated wells vs. that of untreated wells.

The term "pharmaceutically effective amount", as used herein, represents an amount of a compound which is capable of inhibiting leukocyte adherence at vascular cells in mammals. The particular dose of compound administered according to this invention will, of course, be determined by the particular circumstances surrounding the case, including the compound administered, the route of administration, the particular condition being treated, and similar conditions. The compounds can be administered by a variety of routes including the oral, rectal, transdermal, subcutaneous, intravenous, intramuscular or intranasal routes. A typical daily dose will contain from about 0.01 mg/kg to about 80 mg/kg of the active compound of this invention. Preferred daily doses will be about 0.05 to about 10 mg/kg, ideally about 0.1 to about 5 mg/kg.

The compounds of formula I are preferably formulated prior to administration. Therefore, yet another embodiment of the present invention is a pharmaceutical composition comprising a compound of formula I and one or more pharmaceutically acceptable carriers, diluents or excipients therefor.

The present pharmaceutical compositions are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 0.5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

|  | Quantity (mg/capsule) |
| --- | --- |
| active ingredient | 250 |
| starch, dried | 200 |
| magnesium stearate | 10 |
| Total | 460 |

The above ingredients are mixed and filled into hard gelatin capsules in 460 mg quantities.

Formulation 2

Tablets are prepared using the following ingredients:

|  | Quantity (mg/capsule) |
| --- | --- |
| active ingredient | 250 |
| cellulose, microcrystalline | 400 |
| silicone dioxide, fumed | 10 |
| stearic acid | 5 |
| Total | 665 |

The components are blended and compressed to form tablets each weighing 665 mg.

Formulation 3

An aerosol solution is prepared containing the following components:

|  | Weight % |
| --- | --- |
| active ingredient | 0.25 |
| ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| active ingredient | 60 mg |
| --- | --- |
| starch | 45 mg |
| microcrystalline cellulose | 35 mg |
| polyvinylpyrrolidone (as 10% solution in water) | 4 mg |
| sodium carboxylmethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| active ingredient | 80 mg |
| --- | --- |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve and filled into hard gelatin capsules in 200 mg quantities.

Formulation 6

Suppositories each containing 225 mg of active ingredient may be made as follows:

| active ingredient | 225 mg |
| --- | --- |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| active ingredient | 50 mg |
| --- | --- |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| active ingredient | 250 mg |
| --- | --- |
| isotonic saline | 1000 ml |

The solution of the above ingredients is administered intravenously at a rate of 1 ml per minute to a subject in need of treatment.

We claim:

1. A method of inhibiting leukocyte adherence to vascular cells in mammals which comprises administering to a mammal requiring inhibition of leukocyte adherence at its vascular cell a pharmaceutical amount of a compound of the formula I:

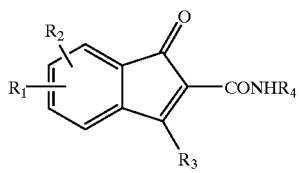

where $R_1$ and $R_2$ are each independently hydrogen, hydroxy, nitro, amino, $C_1$–$C_4$ alkyl, $C_1$–$C_4$ alkoxy or halo;

$R_3$ is hydrogen, hydroxy, $C_1$–$C_6$ alkyl, $C_2$–$C_6$ alkenyl, $C_2$–$C_6$ alkynyl, $C_3$–$C_6$ cycloalkyl, $C_1$–$C_6$ alkoxy, halo, halo ($C_1$–$C_6$ alkyl), unsubstituted or substituted phenyl; and $R_4$ is hydrogen or $C_1$–$C_4$ alkyl, or a pharmaceutically acceptable salt on solvate thereof.

2. The method of claim 1 employing 2-carboxamido-3-pentylindenone or a pharmaceutically acceptable salt or solvate thereof.

3. The method of claim 1 employing 2-carboxamido-3-isopropylindenone or a pharmaceutically salt or solvate thereof.

4. The method of claim 1 employing 2-carboxamido-3-phenylindenone or a pharmaceutically salt or solvate thereof.

5. The method of claim 1 employing carboxamido-3-(3-chloropropyl)indenone or a pharmaceutically salt or solvate thereof.

6. The method of claim 1 employing carboxamido-3-ethylindenone or a pharmaceutically salt or solvate thereof.

7. A method of treating inflammatory disease in a mammal comprising administering to a mammal in need of treatment from inflammatory disease an anti-inflammatory amount of a compound of the formula I:

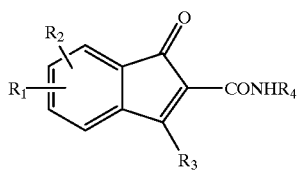

where $R_1$ and $R_2$ are each independently hydrogen, hydroxy, nitro, amino, $C_1$–$C_4$ alkyl, $C_1$–$C_4$ alkoxy or halo;

$R_3$ is hydrogen, hydroxy, $C_1$–$C_6$ alkyl, $C_2$–$C_6$ alkenyl, $C_2$–$C_6$ alkynyl, $C_3$–$C_6$ cycloalkyl, $C_1$–$C_6$ alkoxy, halo, halo ($C_1$–$C_4$ alkyl), unsubstituted or substituted phenyl; and $R_4$ is hydrogen or $C_1$–$C_4$ alkyl, or a pharmaceutically acceptable salt thereof.

8. The method of claim 7 employing 2-carboxamido-3-pentylindenone or a pharmaceutically acceptable salt or solvate thereof.

9. The method of claim 7 employing 2-carboxamido-3-isopropylindenone or a pharmaceutically salt or solvate thereof.

10. The method of claim 7 employing 2-carboxamido-3-phenylindenone or a pharmaceutically salt or solvate thereof.

11. The method of claim 7 employing carboxamido-3-(3-chloropropyl)indenone or a pharmaceutically salt or solvate thereof.

12. The method of claim 7 employing carboxamido-3-ethylindenone or a pharmaceutically salt or solvate thereof.

13. A method of treating rheumatoid arthritis in a mammal which comprises administering to a mammal requiring such treatment, a pharmaceutical amount of a compound of the formula I:

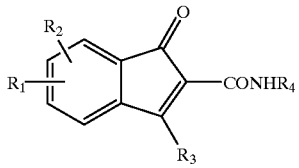

where $R_1$ and $R_2$ are each independently hydrogen, hydroxy, nitro, amino, $C_1$–$C_4$ alkyl, $C_1$–$C_4$ alkoxy or halo;

$R_3$ is hydrogen, hydroxy, $C_1$–$C_6$ alkyl, $C_2$–$C_6$ alkenyl, $C_2$–$C_6$ alkynyl, $C_3$–$C_6$ cycloalkyl, $C_1$–$C_6$ alkoxy, halo, halo($C_1$–$C_6$ alkyl), unsubstituted or substituted phenyl; and $R_4$ is hydrogen or $C_1$–$C_4$ alkyl, or a pharmaceutically acceptable salt or solvate thereof.

14. A method of treating asthma in a mammal which comprises administering to a mammal requiring such treatment, a pharmaceutical amount of a compound of the formula I:

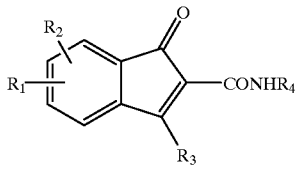

where $R_1$ and $R_2$ are each independently hydrogen, hydroxy, nitro, amino, $C_1$–$C_4$ alkyl, $C_1$–$C_4$ alkoxy or halo;

$R_3$ is hydrogen, hydroxy, $C_1$–$C_6$ alkyl, $C_2$–$C_6$ alkenyl, $C_2$–$C_6$ alkynyl, $C_3$–$C_6$ cycloalkyl, $C_1$–$C_6$ alkoxy, halo, halo($C_1$–$C_6$ alkyl), unsubstituted or substituted phenyl; and $R_4$ is hydrogen or $C_1$–$C_4$ alkyl, or a pharmaceutically acceptable salt or solvate thereof.

15. A method of treating psoriasis in a mammal which comprises administering to a mammal requiring such treatment, a pharmaceutical amount of a compound of the formula I:

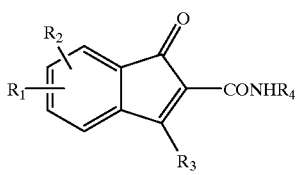

where $R_1$ and $R_2$ are each independently hydrogen, hydroxy, nitro, amino, $C_1$–$C_4$ alkyl, $C_1$–$C_4$ alkoxy or halo;

$R_3$ is hydrogen, hydroxy, $C_1$–$C_6$ alkyl, $C_2$–$C_6$ alkenyl, $C_2$–$C_6$ alkynyl, $C_3$–$C_6$ cycloalkyl, $C_1$–$C_6$ alkoxy, halo, halo($C_1$–$C_6$ alkyl), unsubstituted or substituted phenyl; and $R_4$ is hydrogen or $C_1$–$C_4$ alkyl, or a pharmaceutically acceptable salt or solvate thereof.

16. A method of treating respiratory distress syndrome in a mammal which comprises administering to a mammal requiring such treatment, a pharmaceutical amount of a compound of the formula I:

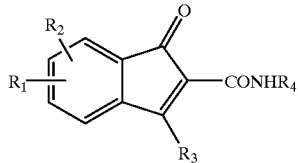

where $R_1$ and $R_2$ are each independently hydrogen, hydroxy, nitro, amino, $C_1$–$C_4$ alkyl, $C_1$–$C_4$ alkoxy or halo;

$R_3$ is hydrogen, hydroxy, $C_1$–$C_6$ alkyl, $C_2$–$C_6$ alkenyl, $C_2$–$C_6$ alkynyl, $C_3$–$C_6$ cycloalkyl, $C_1$–$C_6$ alkoxy, halo, halo($C_1$–$C_6$ alkyl), unsubstituted or substituted phenyl; and $R_4$ is hydrogen or $C_1$–$C_4$ alkyl, or a pharmaceutically acceptable salt or solvate thereof.

17. A method of treating reperfusion injury in a mammal which comprises administering to a mammal requiring such treatment, a pharmaceutical amount of a compound of the formula I:

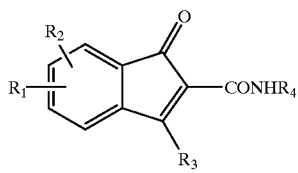

where $R_1$ and $R_2$ are each independently hydrogen, hydroxy, nitro, amino, $C_1$–$C_4$ alkyl, $C_1$–$C_4$ alkoxy or halo;

$R_3$ is hydrogen, hydroxy, $C_1$–$C_6$ alkyl, $C_2$–$C_6$ alkenyl, $C_2$–$C_6$ alkynyl, $C_3$–$C_6$ cycloalkyl, $C_1$–$C_6$ alkoxy, halo, halo($C_1$–$C_6$ alkyl), unsubstituted or substituted phenyl; and $R_4$ is hydrogen or $C_1$–$C_4$ alkyl, or a pharmaceutically acceptable salt or solvate thereof.

18. A method of treating ischemia in a mammal which comprises administering to a mammal requiring such treatment, a pharmaceutical amount of a compound of the formula I:

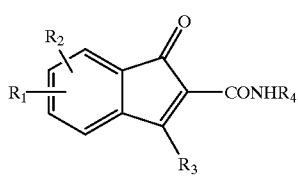

where $R_1$ and $R_2$ are each independently hydrogen, hydroxy, nitro, amino, $C_1$–$C_4$ alkyl, $C_1$–$C_4$ alkoxy or halo;

$R_3$ is hydrogen, hydroxy, $C_1$–$C_6$ alkyl, $C_2$–$C_6$ alkenyl, $C_2$–$C_6$ alkynyl, $C_3$–$C_6$ cycloalkyl, $C_1$–$C_6$ alkoxy, halo, halo($C_1$–$C_6$ alkyl), unsubstituted or substituted phenyl; and $R_4$ is hydrogen or $C_1$–$C_4$ alkyl, or a pharmaceutically acceptable salt or solvate thereof.

19. A method of treating ulcerative colitis in a mammal which comprises administering to a mammal requiring such treatment, a pharmaceutical amount of a compound of the formula I:

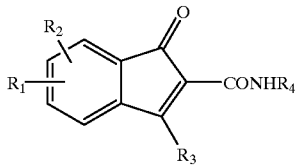

where $R_1$ and $R_2$ are each independently hydrogen, hydroxy, nitro, amino, $C_1$–$C_4$ alkyl, $C_1$–$C_4$ alkoxy or halo;

$R_3$ is hydrogen, hydroxy, $C_1$–$C_6$ alkyl, $C_2$–$C_6$ alkenyl, $C_2$–$C_6$ alkynyl, $C_3$–$C_6$ cycloalkyl, $C_1$–$C_6$ alkoxy, halo, halo ($C_1$–$C_6$ alkyl), unsubstituted or substituted phenyl; and $R_4$ is hydrogen or $C_1$–$C_4$ alkyl, or a pharmaceutically acceptable salt or solvate thereof.

20. A method of treating vasculitis in a mammal which comprises administering to a mammal requiring such treatment, a pharmaceutical amount of a compound of the formula I:

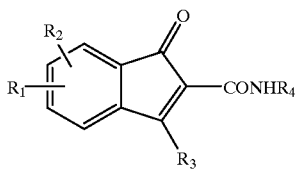

where $R_1$ and $R_2$ are each independently hydrogen, hydroxy, nitro, amino, $C_1$–$C_4$ alkyl, $C_1$–$C_4$ alkoxy or halo;

$R_3$ is hydrogen, hydroxy, $C_1$–$C_6$ alkyl, $C_2$–$C_6$ alkenyl, $C_2$–$C_6$ alkynyl, $C_3$–$C_6$ cycloalkyl, $C_1$–$C_6$ alkoxy, halo, halo ($C_1$–$C_6$ alkyl), unsubstituted or substituted phenyl; and $R_4$ is hydrogen or $C_1$–$C_4$ alkyl, or a pharmaceutically acceptable salt or solvate thereof.

21. A method of treating inflammatory bowel disease in a mammal which comprises administering to a mammal requiring such treatment, a pharmaceutical amount of a compound of the formula I:

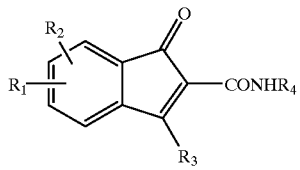

where $R_1$ and $R_2$ are each independently hydrogen, hydroxy, nitro, amino, $C_1$–$C_4$ alkyl, $C_1$–$C_4$ alkoxy or halo;

$R_3$ is hydrogen, hydroxy, $C_1$–$C_6$ alkyl, $C_2$–$C_6$ alkenyl, $C_2$–$C_6$ alkynyl, $C_3$–$C_6$ cycloalkyl, $C_1$–$C_6$ alkoxy, halo, halo ($C_1$–$C_6$ alkyl), unsubstituted or substituted phenyl; and $R_4$ is hydrogen or $C_1$–$C_4$ alkyl, or a pharmaceutically acceptable salt or solvate thereof.

22. A pharmaceutical formulation comprising a compound of the formula I

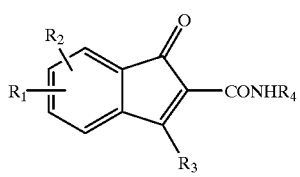

where $R_1$ and $R_2$ are each independently hydrogen, hydroxy, nitro, amino, $C_1$–$C_4$ alkyl, $C_1$–$C_4$ alkoxy or halo;

$R_3$ is hydrogen, hydroxy, $C_1$–$C_6$ alkyl, $C_2$–$C_6$ alkenyl, $C_2$–$C_6$ alkynyl) $C_3$–$C_6$ cycloalkyl, $C_1$–$C_6$ alkoxy, halo, halo ($C_1$–$C_6$ alkyl), unsubstituted or substituted phenyl; and $R_4$ is hydrogen or $C_1$–$C_4$ alkyl, or a pharmaceutically acceptable salt thereof and one or more pharmaceutically acceptable carriers, diluents, or excipients therefor.

23. The pharmaceutical formulation of claim 22 employing 2-carboxamido-3-pentylindenone or a pharmaceutically acceptable salt or solvate thereof.

24. The pharmaceutical formulation of claim 22 employing 2-carboxamido-3-isopropylindenone or a pharmaceutically acceptable salt or solvate thereof.

25. The pharmaceutical formulation of claim 22 employing 2-carboxamido-3-phenylindenone or a pharmaceutically acceptable salt or solvate thereof.

26. The pharmaceutical formulation of claim 22 employing carboxamido-3-(3-chloropropyl)indenone or a pharmaceutically acceptable salt or solvate thereof.

27. The pharmaceutical formulation of claim 22 employing carboxamido-3-ethylindenone or a pharmaceutically acceptable salt or solvate thereof.

* * * * *